US006136582A

United States Patent [19]
Gao et al.

[11] Patent Number: 6,136,582
[45] Date of Patent: Oct. 24, 2000

[54] REVERSE TRANSCRIPTASE OF MOLONEY MURINE LEUKEMIA VIRUS WITH RNA POLYMERASE ACTIVITY

[75] Inventors: Guangxia Gao, Bronx, N.Y.; Stephen P. Goff, Tenafly, N.J.

[73] Assignee: The Trustees of Columbia University in the City, New York, N.Y.

[21] Appl. No.: 09/009,521

[22] Filed: Jan. 20, 1998

[51] Int. Cl.[7] ................................................. C12N 9/12
[52] U.S. Cl. ............................................................ 435/194
[58] Field of Search ............................................. 435/194

[56] References Cited

PUBLICATIONS

Arnold, E. et al., (1995) "Structures of DNA and RNA Polymerases and Their Interactions With Nucleic Acid Substrates," *Current Opinion In Structural Biology*, 5(1):27–38.(Exhibit 1).
Baltimore, D., (1970) "Viral RNA–dependent DNA Polymerase," *Nature*, 226(5252): 1209–1211 (Exhibit 2).
Delarue, M. et al., (1990) "An Attempt to Unify the Structure of Polymerases," *Protein Eng.*, 3(6):461–467. (Exhibit 3).
Georgiadis, M.M. et al., (1995) "Mechanistic Implications From the Structure of a Catalytic Fragment of Moloney Murine Leukemia Virus Reverse Transcriptase," *Structure*, (London), 3(9):879–892. (Exhibit 4).
Goff, S. et al., (1981) "Isolation and Properties of Moloney Murine Leukemia Virus Mutants: Use of a Rapid Assay for Release of Virion Reverse Transcriptase," *J. Virology*, 38(1):239–248. (Exhibit 5).
Joyce, C.M. and Steitz, T.A.,–(1994) "Function and Structure Relationships in DNA Polymerases," *Annu. Rev. Biochem.*, 63:777–822. (Exhibit 6).
Joyce, C.M., (1997) "Choosing the Right Sugar: How Polymerases Select a Nucleotide Substrate," *Proc. Natl. Acad. Sci. USA*, 94(5):1619–1622. (Exhibit 7).
Patel, P.H. et al., (1995) "Insights Into DNA Polymerization Mechanisms From Structure and Function Analysis of HIV–1 Reverse Transcriptase," *Biochemistry*, 34(16):5351–5363. (Exhibit 8).
Sousa, R. et al., (1993) "Crystal Structure of Bacteriophage T7 RNA Polymerase at 3.3 Å Resolution," *Nature*, 364(6438):593–599. (Exhibit 9).
Sousa, R. and Padilla, R., (1995) "A Mutant T7 RNA Polymerase as a DNA Polyerase," *EMBO J.*, 14(18):4609–4621. (Exhibit 10).
Steitz, T.A. et al., (1994) "A Unified Polymerase Mechanism for Nonhomologous DNA and RNA Polymerases," *Science*, 266(5913):2022–2025. (Exhibit 11).
Temin, H. and Mizutani, S., (1970) "RNA–dependent DNA Polymerase in Virions of Rous Sarcoma Virus," *Nature*, (London), 226(5252):1211–1213. (Exhibit 12).
Gao, Guangxia, et al. (1997) Proc Natl. Acad, Sci, USA 94, 407–411.

*Primary Examiner*—Charles L. Patterson, Jr.
*Attorney, Agent, or Firm*—John P. White; Cooper & Dunham LLP

[57] ABSTRACT

This invention provides a polypeptide capable of polymerizing i) deoxyribonucleotides; ii) ribonucleotides; or iii) one or more deoxyribonucleotides and one or more ribonucleotides. This invention further provides a purified Moloney murine leukemia virus reverse transcriptase, wherein an amino acid corresponding to position 155 of a wild type Moloney murine leukemia virus reverse transcriptase is a valine. This invention also provides a method of polymerizing a nucleic acid molecule comprising one or more deoxyribonucleotides and one or more ribonucleotides comprising: contacting a polypeptide capable of polymerizing i) deoxyribonucleotides; ii) ribonucleotides; or iii) one or more deoxyribonucleotides and one or more ribonucleotides with deoxyribonucleotides and ribonucleotides under conditions permitting incorporation of deoxyribonucleotides and ribonucleotides into a nucleic acid molecule. This invention still further provides a method of converting a DNA polymerase into an RNA polymerase comprising: a) structurally modifying the DNA polymerase; b) contacting the structurally modified DNA polymerase of step (a) with deoxyribonucleotides and ribonucleotides under conditions permitting incorporation of deoxyribonucleotides and ribonucleotides into a nucleic acid molecule; and c) detecting polymerization of ribonucleotides in the nucleic acid molecule resulting from step (b), the detection of ribonucleotides in the polymerized nucleic acid molecule indicating that the structurally modified DNA polymerase has been converted into an RNA polymerase. This invention also provides a nucleic acid molecule polymerized by the above-described method of polymerizing a nucleic acid molecule comprising one or more deoxyribonucleotides and one or more ribonucleotides.

3 Claims, 6 Drawing Sheets

REVERSE TRANSCRIPTASE OF MOLONEY MURINE LEUKEMIA VIRUS WITH RNA POLYMERASE ACTIVITY

STATEMENT REGARDING FEDERALLY FUNDED RESEARCH

The invention disclosed herein was made with Government support under NIH Grant No. CA 30488. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

The traditional classification of nucleic acid polymerases as either DNA or RNA polymerases is based, in large part, on their fundamental preference for the incorporation of either deoxyribonucleotides or ribonucleotides during chain elongation. The refined structure determination of Moloney murine leukemia virus reverse transcriptase, a strict DNA polymerase, recently allowed the prediction that a single amino acid residue at the active site might be responsible for the discrimination against the 2'OH group of an incoming ribonucleotide. Mutation of this residue resulted in a variant enzyme now capable of acting as an RNA polymerase. In marked contrast to the wild-type enzyme, the $K_m$ of the mutant enzyme for ribonucleotides was comparable to that for deoxyribonucleotides. The results are consistent with proposals of a common evolutionary origin for both classes of enzymes, and support models of a common mechanism of nucleic acid synthesis underlying catalysis by all such polymerases.

A key characteristic of nucleic acid polymerases is their traditional classification as either DNA or RNA polymerases, which is determined by a given enzyme's ability to selectively use either deoxyribonucleotides (dNTPs) or ribonucleotides (rNTPs) as substrates for incorporation into a growing chain (1, 2). This classification, however, may not be as fundamental as originally thought (3–5). Crystallographic studies have demonstrated that DNA and RNA polymerases have remarkable structural similarities (refs. 6–15, reviewed in ref. 16), even though they lack extensive primary sequence homology. Both have a characteristic protein fold forming a nucleic acid binding cleft, and a trio of carboxylic acid residues thought to participate directly in catalysis through two bound divalent metal ions. Steady-state analyses further support the notion of a common stepwise polymerization mechanism (17, 18). These observations suggest that it might be possible to convert a DNA polymerase into an RNA polymerase by relatively minor alterations in its structure.

Reverse transcriptases (RTs), encoded by all retroviruses, play a defining role in the retroviral life cycle (refs 19 & 20; for reviews see ref. 21). The enzyme is responsible for the synthesis of a double-stranded linear DNA copy of the RNA genome, which is subsequently inserted into the host genome to form the integrated proviral DNA. The reverse transcription reaction is complex, requiring RNA-dependent DNA polymerase activity, DNA-dependent DNA polymerase activity, and an associated RNase activity specific for RNA in RNA:DNA hybrid form (22). Although the enzyme can copy either RNA or DNA templates, RT, like all DNA polymerases, can only use deoxyribonucleotides, and not ribonucleotides as substrates. Studies of the HIV-1 RT have permitted modeling of the position of the incoming nucleotide at the active site (23, 24), with α-helices C and E, and β-sheet strands 6, and 9–11, setting the major topology of the dNTP binding site. A recently determined crystal structure of a catalytic fragment of Moloney murine leukemia virus (MMLV) RT at 1.8 Å resolution has made it possible to visualize how such selectivity for deoxyribonucleotides might be achieved: the enzyme is proposed to discriminate against ribonucleotides through an unfavorable interaction between the aromatic ring of Phe-155 and the 2'OH of the incoming rNTP (ref. 14; see FIG. 1). Here we report that substitution of this residue by valine, as predicted, does indeed render the enzyme capable of incorporating ribonucleotide substrates into products.

SUMMARY OF THE INVENTION

This invention provides a polypeptide capable of polymerizing i) deoxyribonucleotides; ii) ribonucleotides; or iii) one or more deoxyribonucleotides and one or more ribonucleotides.

This invention further provides a purified Moloney murine leukemia virus reverse transcriptase, wherein an amino acid corresponding to position 155 of a wild type Moloney murine leukemia virus reverse transcriptase is a valine.

This invention also provides a method of polymerizing a nucleic acid molecule comprising one or more deoxyribonucleotides and one or more ribonucleotides comprising: contacting a polypeptide capable of polymerizing i) deoxyribonucleotides; ii) ribonucleotides; or iii) one or more deoxyribonucleotides and one or more ribonucleotides with deoxyribonucleotides and ribonucleotides under conditions permitting incorporation of deoxyribonucleotides and ribonucleotides into a nucleic acid molecule.

This invention still further provides a method of converting a DNA polymerase into an RNA polymerase comprising: a) structurally modifying the DNA polymerase; b) contacting the structurally modified DNA polymerase of step (a) with deoxyribonucleotides and ribonucleotides under conditions permitting incorporation of deoxyribonucleotides and ribonucleotides into a nucleic acid molecule; and c) detecting polymerization of ribonucleotides in the nucleic acid molecule resulting from step (b), the detection of ribonucleotides in the polymerized nucleic acid molecule indicating that the structurally modified DNA polymerase has been converted into an RNA polymerase.

This invention also provides a nucleic acid molecule polymerized by the above-described method of polymerizing a nucleic acid molecule comprising one or more deoxyribonucleotides and one or more ribonucleotides.

DETAILED DESCRIPTION OF THE INVENTION

Figure 1:
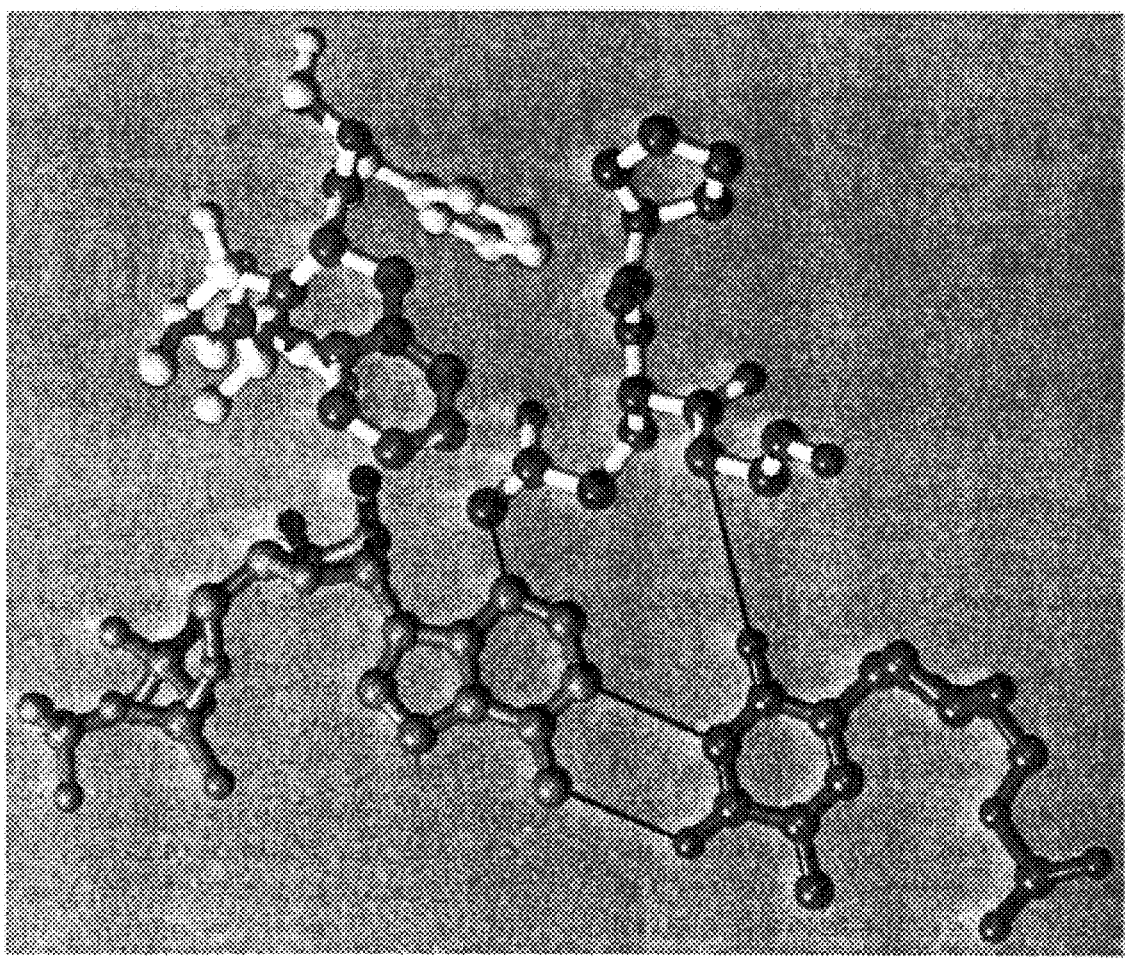
FIG. 1. Modeling of interactions between the MMLV RT, DNA, and rATP at the polymerase active site. A ball-and-stick representation of the minor groove hydrogen-bonding interactions is shown for the modeled ternary complex. Residues 189–191 are shown in red, residues 153, 154, and 156 in yellow, F155 in magenta, rATP in orange, and dT in green. F155 is shown directly below the 2'OH of rATP, serving to discriminate between ribose- and deoxyribose-containing nucleotides.

This invention provides a polypeptide capable of polymerizing i) deoxyribonucleotides; ii) ribonucleotides; or iii) one or more deoxyribonucleotides and one or more ribonucleotides.

In a preferred embodiment of the invention, the polypeptide has an amino acid sequence encoding a portion of a reverse transcriptase wherein the amino acid corresponding to position 155 of the wild type reverse transcriptase is a valine. In another preferred embodiment of the invention, the polypeptide is a nucleic acid polymerase. In a further preferred embodiment of the invention, the nucleic acid polymerase is a reverse transcriptase. In a most preferred embodiment of the invention, the reverse transcriptase is a Moloney murine leukemia virus reverse transcriptase.

As used herein a nucleic acid polymerase is defined as a polypeptide which incorporates either deoxyribonucleotides or ribonucleotides into a growing chain of a nucleic acid molecule under appropriate polymerization conditions. A nucleic acid polymerase may be a DNA polymerase or an RNA polymerase. Synthesis of a nucleic acid molecule using a nucleic acid polymerase occurs by extension of a primer. The primer can be either DNA or RNA. The primer is annealed to a template strand, which may be either DNA or RNA. The sequence of the nucleic acid polymerized [added] to the primer is determined by the template. For reverse transcriptases the template can be either RNA or DNA.

The nucleic acid polymerase of the subject invention differs from known nucleic acid polymerases by the ability to polymerize a nucleic acid molecule product which comprises RNA, DNA, or a hybrid of RNA and DNA.

The composition of the polymerized nucleic acid molecule product is determined by the substrates present for polymerization, i.e., ribonucleotides, deoxynucleotides, or a combination of ribonucleotides and deoxynucleotides, and the template used. The substrates are present in concentrations permitting polymerization by the nucleic acid polymerase.

This invention provides a purified Moloney murine leukemia virus reverse transcriptase, wherein an amino acid corresponding to position 155 of a wild type Moloney murine leukemia virus reverse transcriptase is a valine.

In a preferred embodiment of the invention the purified Moloney murine leukemia virus reverse transcriptase is capable of polymerizing i) deoxyribonucleotides; ii) ribonucleotides; or iii) one or more deoxyribonucleotides and one or more ribonucleotides.

This invention provides a method of polymerizing a nucleic acid molecule comprising one or more deoxyribonucleotides and one or more ribonucleotides comprising: contacting a polypeptide capable of polymerizing i) deoxyribonucleotides; ii) ribonucleotides; or iii) one or more deoxyribonucleotides and one or more ribonucleotides with deoxyribonucleotides and ribonucleotides under conditions permitting incorporation of deoxyribonucleotides and ribonucleotides into a nucleic acid molecule. Appropriate nucleic acid synthesis conditions which permit incorporation of deoxyribonucleotides and ribonucleotides into a nucleic acid molecule are known to one of skill in the art and include, but are not limited to, the presence of appropriate buffers and appropriate concentrations of substrates for the nucleic acid molecules to be produced. Suitable substrates may be deoxyribonucleotides (dNTPs), ribonucleotides (rNTPs), or a mixture of dNTPs and rNTPs.

In a preferred embodiment of the above-described method of polymerizing a nucleic acid molecule comprising one or more deoxyribonucleotides and one or more ribonucleotides, the polypeptide has an amino acid sequence encoding a portion of a reverse transcriptase wherein the amino acid corresponding to position 155 of the wild type reverse transcriptase is a valine. In a further preferred embodiment the polypeptide is a nucleic acid polymerase. In a still further preferred embodiment the polypeptide is a reverse transcriptase. In a most preferred embodiment the reverse transcriptase is a Moloney murine leukemia virus reverse transcriptase. In another preferred embodiment of the above-described method the polymerized nucleic acid molecule is a ribozyme.

The nucleic acid products may be any RNA molecule, any DNA molecule or a hybrid molecule of RNA and DNA. The nucleic acid sequence of the polymerization product is determined by the template nucleic acid strand which the nucleic acid polymerase uses to add bases, e.g. dNTPs, rNTPs or both dNTPs and rNTPs, to the primer which is annealed to the template.

In a further preferred embodiment of the above-described method the polymerized nucleic acid molecule has at least one specific cleavage site.

For example, a polymerized nucleic acid molecule may be comprised of DNAs with only one ribonucleotide polymerized within the nucleic acid strand. Such a hybrid nucleic acid molecule can be cleaved at the ribonucleotide under alkaline conditions. Accordingly, nucleic acid molecules with a specific cleavage site may be synthesized by the above-described nucleic acid polymerase. Alternatively, nucleic acid molecules having more than one specific cleavage site may also be produced using the above-described nucleic acid polymerase. The nucleic acid sequence is determined by the template used by the nucleic acid polymerase and the substrates used in the polymerization.

This invention provides a method of converting a DNA polymerase into an RNA polymerase comprising: a) structurally modifying the DNA polymerase; b) contacting the structurally modified DNA polymerase of step (a) with deoxyribonucleotides and ribonucleotides under conditions permitting incorporation of deoxyribonucleotides and ribonucleotides into a nucleic acid molecule; and c) detecting polymerization of ribonucleotides in the nucleic acid molecule resulting from step (b), the detection of ribonucleotides in the polymerized nucleic acid molecule indicating that the structurally modified DNA polymerase has been converted into an RNA polymerase.

In preferred embodiment of the above-described method the structural modification of the DNA polymerase in step (a) is performed by a point mutation or by polymerase chain reaction (PCR). In another preferred embodiment of the above-described method the point mutation or the polymerase chain reaction substitutes an amino acid corresponding to position 155 of a wild type DNA polymerase for a valine.

Methods of altering the amino acid structure of enzymes, including DNA polymerases, are well known to one of ordinary skill in the art. These methods include, but are not limited to, point mutation and polymerase chain reaction, PCR, e.g. as described in Kunkel et al. Methods Enzymol. 155, 166 (1987) and Ausubel et al. Current Protocols in Molecular Biology (1987), John Wiley/Greene.

In a most preferred embodiment of the above-described method of converting a DNA polymerase into an RNA polymerase the DNA polymerase is a Moloney murine leukemia virus reverse transcriptase.

This invention provides a nucleic acid molecule polymerized by the above-described method of polymerizing a nucleic acid molecule comprising one or more deoxyribonucleotides and one or more ribonucleotides. In a preferred embodiment the polymerized nucleic acid molecule has at least one specific cleavage site. In a further preferred embodiment the polymerized nucleic acid molecule is capable of digesting a nucleic acid molecule. In a most preferred embodiment the polymerized nucleic acid molecule is a ribozyme.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Construction of RT Mutants. The RNase H-defective MMLV reverse transcriptase construct (RT-WT-H) has been described previously (25). RT-F155V-H was constructed by replacing a KpnI-SalI fragment of RT-WT-H (nucleotides 261–1108) with KpnI-AflII and AflII-SalI PCR-derived MMLV RT fragments. Primer F155V-sense (5'-ATATAG CTTAAGGATGCCGTTTTCTGCCTGAGACTCCAC-3') (SEQ ID NO. 1), bearing the mutant valine codon (in boldface type; nucleotides 463–465) and silent mutations creating an AflII site (underlined), and a downstream primer were used to generate the 0.2-kb AflII-SalI PCR fragment, while the F155V-antisense primer (5'-ATATAG CTTAAGATCAAGCACAGTGTACCA-3') (SEQ ID NO. 2), bearing silent mutations to create an AflII site (underlined), and an upstream primer were used to generate the 0.6-kb KpnI-AflII PCR fragment. RT-F155Y-H, in which Phe-155 was substituted by tyrosine, was constructed by replacing the 0.2-kb AflII-SalI fragment of RT-F155V-H with a 0.2-kb AflII-SalI PCR fragment containing a TAT tyrosine codon and an AflII site introduced by the sense primer.

Enzyme Purification. Recombinant RT enzymes were expressed in *Eschericha coli* DH5α and partially purified with DE52 resin as described (26) for use in homopolymer assays. For all other assays, enzymes were purified to near-homogeneity by chromatography on DE52 cellulose (Whatman), P11 phosphocellulose (Whatman), and MonoS (Pharmacia) fast protein liquid chromatography (FPLC).

Homopolymer Substrate Assays. Typical assays were performed using ≈40 ng of enzyme (as determined by immunoblot comparison with pure RT standards) in 50 µl of RT reaction buffer (27) containing 60 mM Tris.HCl (pH 8.0), 75 mM NaCl, 0.7 mM $MnCl_2$, 5 mM DTT, 12 µg/ml homopolymer template, 6 µg/ml oligonucleotide primer, 10 µCi/ml (1 Ci=37 GBq) $^{32}P$-labeled nucleotide and 12 µM unlabeled nucleotide substrate.

Measurement of Enzyme Kinetics. Purified enzyme was added to substrates in reaction buffer to initiate the reaction. At each time point, 10 µl of reaction solution was removed and stopped by addition of EDTA. Samples were spotted on DE81 paper (Whatman) and washed with 2× standard saline citrate, followed by scintillation counting. Radioactivity retained on the paper, in comparison with total radioactivity in each sample, was used to determine the amount of dTTP incorporated into the product. Parameters were determined by double reciprocal plot.

Single Nucleotide Extension Assay. Oligonucleotide C14 (5'-GGTTCCTACCGGCC-3') (SEQ ID NO. 3) was end labeled with [γ-$^{32}$P]ATP using polynucleotide kinase (New England Biolabs) according to the manufacturer's specifications. The radiolabeled product oligonucleotide (*C14) was purified by G25 spin column (Boehringer Mannheim) and annealed to G17 (3'-CCAAGGATGGCCGGATC-5') (SEQ ID NO. 4) at room temperature for 0.5 hr. Primer extension was initiated by adding 3 µg of purified enzyme to 60 µl of reaction buffer containing 60 mM Tris.HCl (pH 8.0), 75 mM NaCl, 0.7 mM $MnCl_2$, 5 mM DTT, 0.1 µM *C14/ G17 and unlabeled nucleotide substrate at the indicated concentration. At each time point, 10 µl of the reaction was taken out and mixed with 10 µl stop solution (80% formamide, 0.1% xylene cyanol, 0.1% bromophenol blue, and 0.1 M EDTA). The extension products were resolved by electrophoresis on a 23% urea polyacrylamide gel and detected by autoradiography.

Ribonucleotide Incorporation by RT-F155V-H Using Heteropolymeric Templates. A 0.3-kb PCR fragment, generated by the F155V-antisense primer and the upstream primer, was cloned into pBluescript (Stratagene) by blunt-end ligation, oriented such that the antisense primer sequence was near the T7 promotor in the vector. The plasmid was linearized and transcribed to generate a 0.32-kb RNA fragment by in vitro run-off transcription using T7 RNA polymerase (Boehringer Mannheim) according to the manufacturer's instructions. A 0.3-kb single strand DNA was generated by asymmetric PCR using an excess of the F155V antisense primer. The upstream primer was annealed to either template, at concentrations of 40 nM primer and 50 nM template, and extended by 3 µg of purified enzyme for 30 min at 37° C. in 60 µl of reaction buffer containing 60 mM Tris.HCl (pH 8.0), 75 mM NaCl, 7.5 mM MgCl$_2$, 5 mM DTT, 500 µM dNTPs, 1 unit/ml RNasin and 50 µCi of [$^{32}$P]rNTP. The extended products were precipitated, resuspended in 10 µl stop solution and resolved by electrophoresis on a 5% urea polyacrylamide gel, followed by autoradiography.

Figure 2:
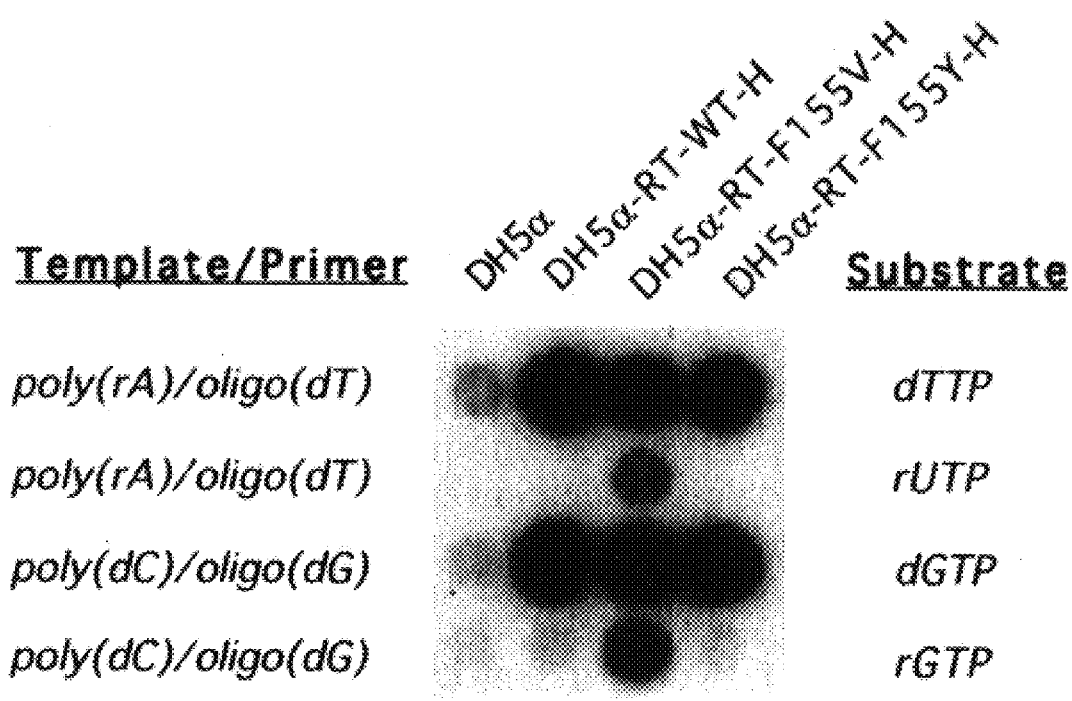
FIG. 2. RT-F155V-H can incorporate rUTP or rGTP into products, using poly(rA)/oligo(dT) or poly(dC)/oligo(dG) as template/primer. Reactions were performed with the indicated template/primer, enzymes, and labeled substrates, and elongated products were assayed by spotting on DE81 paper, washing and autoradiography. Mutant RT-F155V-H was uniquely able to incorporate ribonucleotides.

RNA Synthesis by RT-F155V-H. Primer oligonucleotide P17 (5'AAGCCCCACATACAGAG-3') (SEQ ID NO. 5) was end labeled and annealed to template oligonucleotide T28 (3'-TTCGGGGTGTATGTCTCTGACAACCTGG-5') (SEQ ID NO. 6) as described above. The primer (0.1 µM) was extended by 3 µg of RT-F155V-H per 60 µl using four dNTPs (500 µM each) or rNTPs (500 µM each) as substrates. Products were processed and analyzed as described above.

predicted, the substitution of Phe-155 with valine rendered the enzyme (designated RT-F155V-H) capable of incorporating ribonucleotides into the products from two different templates (FIG. 2). The wild type enzyme was unable to use ribonucleotides, and the tyrosine substitution (designated RT-F155Y-H) did not alter the enzyme's behaviour. Of 20 substitution mutants with changes of unrelated residues also located near the active site, none showed similar effects (data not shown).

Figure 3A:
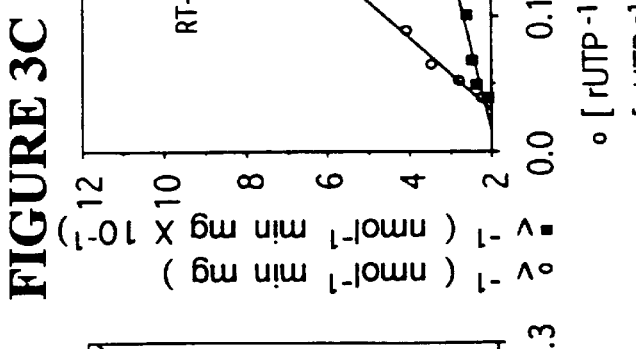
FIGS. 3A–C. Kinetic analysis of RT-WT-H and RT-F155V-H. (3A) Various concentrations of oligo(dT)$_{12}$ primer were annealed to 15 µg/ml poly(rA) template in a reaction buffer containing 60 mM Tris-HCl (pH 8.0), 75 mM NaCl, 0.7 mM MgCl$_2$, 5 mM DTT, 100 µM dTTP and 20 µCi/ml [$^{32}$P]dTTP. Reactions were initiated by adding 800 ng/ml purified enzyme. Data points were taken at 20-sec. intervals. (3B) Reactions were performed in the presence of 15 µg/ml poly(rA), 7.5 µg/ml oligo(dT), 800 ng/ml enzyme, and various concentrations of dTTP and [$^{32}$P]dTTP. Data points were taken at 20 second intervals. (3C) Reactions were performed in the presence of 15 µg/ml poly(rA), 7.5 µg/ml oligo(dT), 8 µg/ml enzyme, and various concentrations of rUTP and [$^{32}$P]rUTP. Data points were taken at intervals of 2 min (for RT-WT-H) or 20 sec (for RT-F155V-H).
Figure 3B:
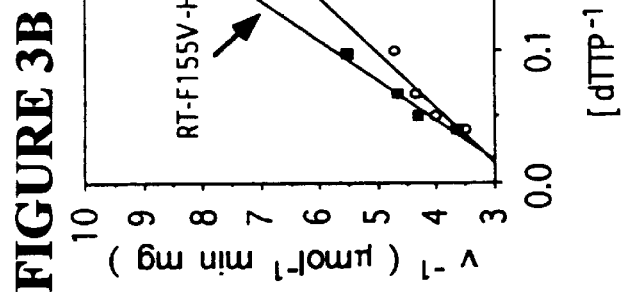
Figure 3C:
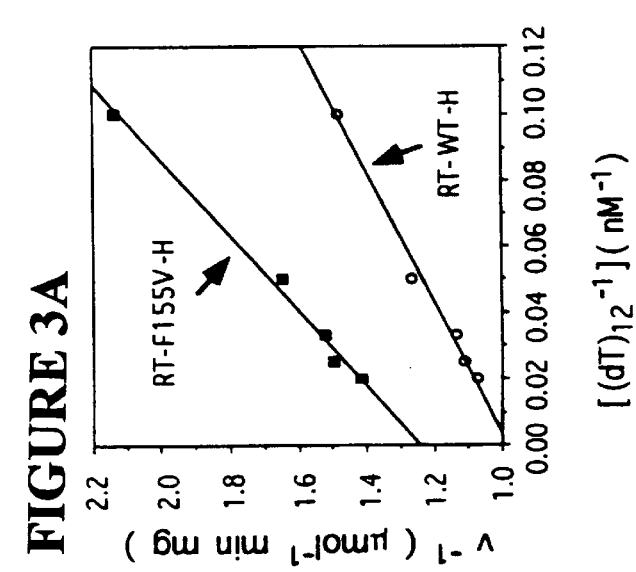

The effect of valine substitution was further analyzed by kinetic measurements of the enzyme activity using purified RTs and poly(rA)/oligo(dT) as template/primer (FIG. 3). The results are summarized in Table 1. RT-F155V-H was similar to RT-WT-H with respect to rate constants ($K_m$) for oligo(dT) and dTTP, as well as maximum velocity (Vmax) using dTTP as a substrate. These similarities between RT-WT-H and RT-F155V-H in these parameters, along with their comparable enzymatic activities on various template/primers under different conditions (data not shown), indicate that the overall structure of RT-F155V-H was hardly, if at all, changed by the substitution. However, the affinity of RT-F155V-H for rUTP was dramatically increased. Whereas the $K_m$ of the wild type enzyme for rUTP was almost 50-fold higher than for dTTP, mutant RT-F155V-H displayed comparable $K_m$ values for rUTP and dTTP (Table 1). These results strongly imply that Phe-155 is a key amino acid that dictates the selective binding of deoxyribonucleotides to the enzyme. Interestingly, the $V_{max}$ of RT-F155V-H for rUTP was only marginally changed compared with the wild-type, remaining ≈100 fold less than for dTTP.

TABLE 1

Summary of kinetic parameters

| | (DT)$_{12}$ | | dTTP | | rUTP | |
|---|---|---|---|---|---|---|
| Enzyme | $V_{max}$ µmol · min$^{-1}$ · mg$^{-1}$ | $K_m$, nM | $V_{max}$ µmol · min$^{-1}$ · mg$^{-1}$ | $K_m$, µM | $V_{max}$ µmol · min$^{-1}$ · mg$^{-1}$ | $K_m$, µM |
| RT-WT-H | 1.02 ± 0.05 | 5.27 ± 1.95 | 0.38 ± 0.07 | 9.2 ± 3.4 | 1.17 ± 0.51 | 443 ± 221 |
| RT-F155 | 0.81 ± 0.06 | 8.27 ± 3.44 | 0.41 ± 0.04 | 13.6 ± 2.4 | 5.45 ± 0.53 | 4.34 ± 1.71 |

EXPERIMENTAL RESULTS AND DISCUSSION

Figure 4A:
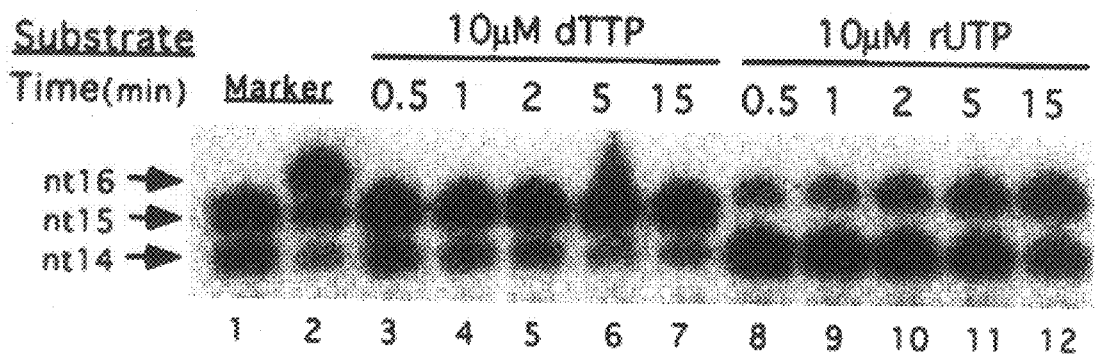
FIGS. 4A–C. Both incorporation and extension of incorporated ribonucleotides by RT-F155V-H are slower than for deoxyribonucleotides. 5' end-radiolabeled 14-mer DNA primer was annealed to a 17-mer DNA template at a 1:1 ratio. (4A) The primer was extended by RT-F155V-H using either 10 µM dTTP or rUTP as a substrate. At the indicated time points, an aliquot of the reaction was removed and analyzed by gel electrophoresis. (4B) The primer was extended by RT-WT-H in the presence of 10 µM dTTP, 10 µM rUTP, or 200 µM rUTP. (4C) The 14-mer primer was first extended by either 10 µM dTTP or 10 µM rUTP to completion. The extended 15-mer primers were then further extended by adding either 10 µM dATP or 10 µM rATP to the reaction. Markers were generated by extending *C14 with ddTTP (nt15) or dTTP puls ddATP (nt16). Products with ribonucleotides at the 3' terminus migrated more slowly than those with deoxyribonucleotides at the terminus. The bands migrating at the position of nt17 (lanes 5–8 and 15–17) presumably resulted from untemplated extension of dATP at the last nucleotide of the template.
Figure 4B:
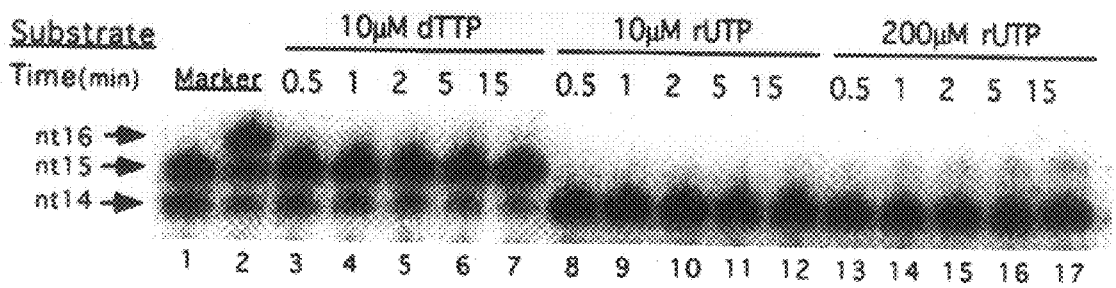
Figure 4C:
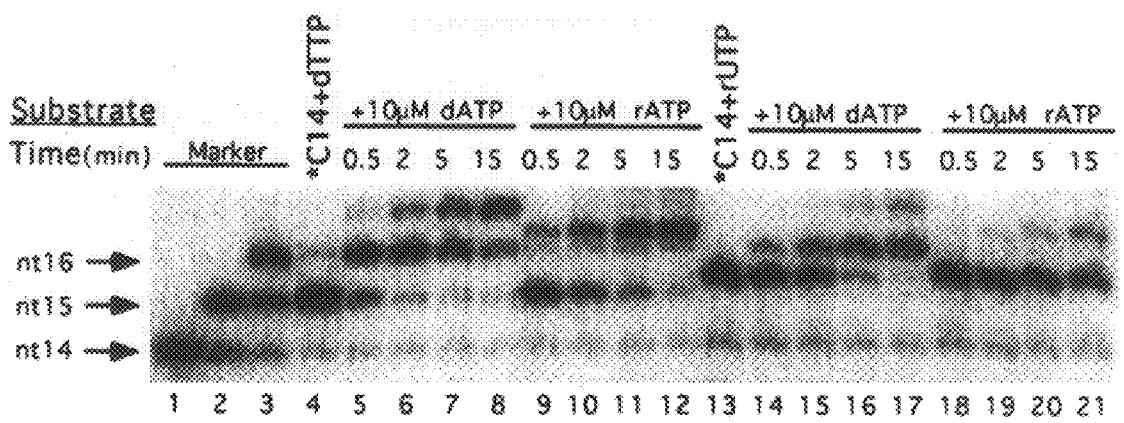

Examination of the active site of a high-resolution structure of the MMLV RT, and modeling of template-primer and substrate into the structure, resulted in a strong prediction that the 2'OH of an incoming rNTP would overlap with the bulky sidegroup of Phe-155 (14). To test the structural prediction, a mutant MMLV RT was constructed carrying a substitution of Phe-155 with valine in the hope that the smaller side chain would open the "door" of the enzyme to ribonucleotides (see Methods). As a control, a mutant was also generated in which Phe-155 was replaced by tyrosine, found at the corresponding position in HIV-RT and thought to play the same role as the phenylalanine in MMLV-RT. In anticipation of potential cleavages of the RNA products by the RNase H activity in MMLV-RT, the substitutions were introduced into an RNase H-defective MMLV-RT backbone (designated RT-WT-H), which contains a mutation from Asp-524 to Asn (28). RT-WT-H lacks almost all RNase H activity but retains DNA polymerase activity comparable to the wild type MMLV-RT (28). Each mutant enzyme was expressed in bacteria, partially purified, and assayed on homopolymer templates with various substrates. As The lower catalytic rate of RT-F155V-H for ribonucleotide substrates could be accounted for by either an inherently lower ribonucleotide incorporation rate, or a lower extension rate of a ribonucleotide-containing primer, or both. To distinguish between these possibilities, a single nucleotide extension assay was performed. As shown in FIG. 4a, the mutant extended ≈75% of the primer by addition of dTTP within 0.5 min, while even after 15 min, only ≈50% of the primer was extended by rUTP. In comparison, RT-WT-H incorporated barely detectable amount of rUTP even at a concentration as high as 200 µM (FIG. 4b). Furthermore, the incorporation of rUTP slowed the catalysis of the following nucleotide, either DATP or rATP, ≈5 fold (FIG. 4c). Products with a 3' terminal ribonucleotide migrated slightly more slowly than those with a deoxyribonucleotide.

Figure 5A:
FIGS. 5A . C. RT-F155V-H incorporates ribonucleotides into products. (5A) A short primer was extended by RT-WT-H (lanes 1, 3, 5, 7, 9) or RT-F155V-H (lanes 2, 4, 6, 8, 10) on a long single-stranded RNA template, in the presence of a mixture of four dNTPs and radiolabeled nucleotides as indicated. (5B) Similar experiment on a single-stranded DNA template. (5C) End-labeled P17 oligonucleotide primer was extended by RT-F155V-H on T28 oligonucleotide template using either four dNTPs or rNTPs as substrates.
Figure 5B:
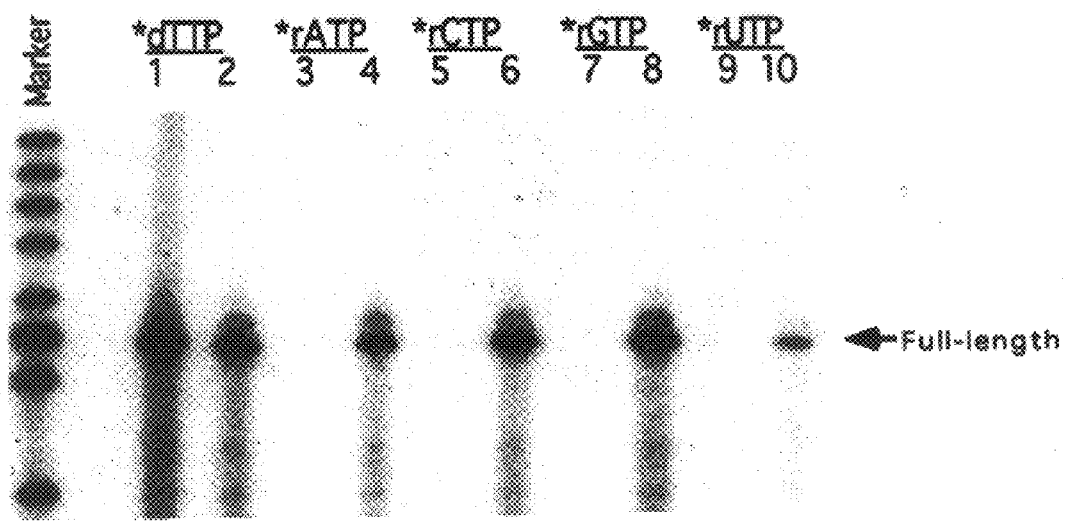

To expand these kinetics analysis results, RT-WT-H and RT-F155V-H were used to copy single-stranded DNA or RNA templates using dNTPs or rNTPs as substrates (FIG. 5). RT-F155V-H incorporated all four ribonucleotides into long products from a mixture of rNTPs and dNTPs, using either DNA (FIG. 5a) or RNA (FIG. 5b) as a template. In contrast, RT-WT-H could barely incorporate detectable ribonucleotides into the product, though it could synthesize DNA products efficiently. That RT-F155V-H had little preference for any particular ribonucleotide substrate supports the specific function of Phe-155 to distinguish ribonucleotides from deoxyribonucleotides.

Figure 5C:
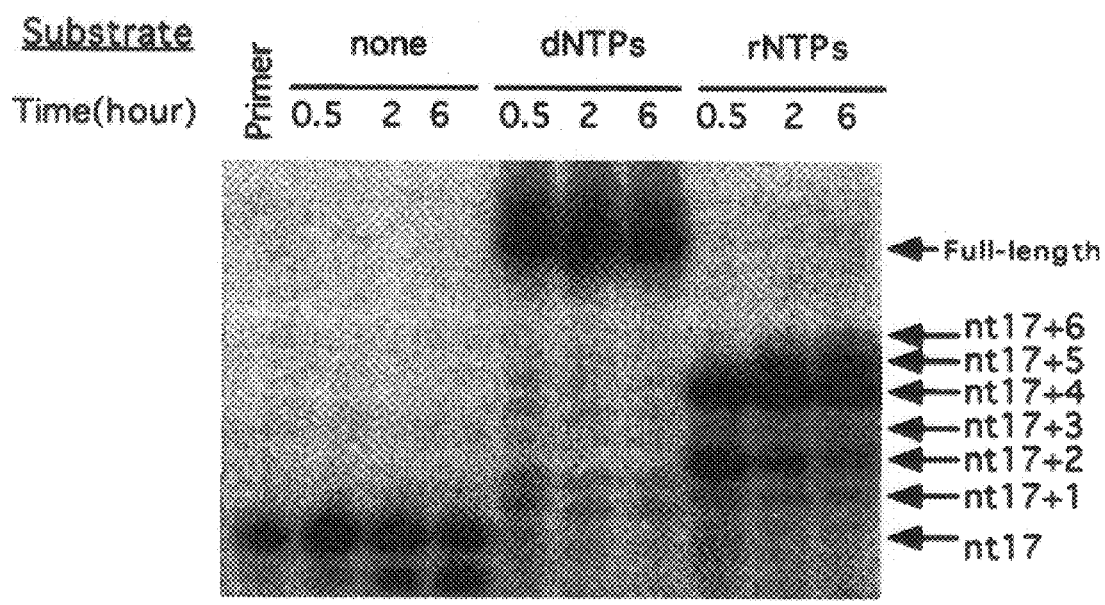

To further evaluate the ability of the enzyme to synthesize RNA, only ribonucleotides were used as substrates (FIG. 5c). Despite the slow ribonucleotide polymerization rate, which is consistent with the kinetics results, RT-F155V-H was able to make an extended product of pure RNA of at least 6 nt under the given conditions. It is worth noting again that the ribonucleotide products migrated slower than the corresponding deoxyribonucleotide ones, indicating that the ribonucleotide products did not come from possible dNTPs contamination in the rNTP preparations.

The results presented above provide direct evidence supporting the common stepwise mechanism of nucleic acid polymerization underlying all nucleotide polymerases catalysis. Such a common catalysis mechanism, along with structural similarities among the polymerases (3, 11, 29), suggests that all nucleotide polymerases might have evolved from the same ancestor. Indeed, this notion is supported by the observation that point mutations in T7 RNA polymerase can result in the reciprocal change in specificity to that observed here; these mutations rendered the enzyme, normally specific for ribonucleotides, capable of incorporating deoxyribonucleotides (16, 30). The mechanism by which these mutations act is unknown. The results also provide insight into how a DNA polymerase selectively uses deoxyribonucleotides as opposed to ribonucleotides as substrates. Multiple devices are employed by the enzyme to prevent incorporation of ribonucleotides, which might be lethal to organisms. In MMLV RT, Phe-155 serves as a door to preclude ribonucleotides from binding to the enzyme; and ribonucleotides, once bound to the enzyme, are further discriminated against by catalytic machinery for both incorporation and extension. It would be interesting to identify sequences governing the catalytic rate of the enzyme to use ribonucleotide substrates, by structure-based mutagenesis or by colony screening following random mutagenesis (31). RT-F155V-H may prove to be a powerful tool to serve this purpose.

REFERENCES

1. Kornberg, A. (1974) *DNA Synthesis* (Freeman, San Francisco).
2. Kornberg, A. & Baker, T. A. (1991) *DNA Replication* (Freeman, New York).
3. Delarue, M., Poch, O., Tordo, N., Moras, D. & Argos, P. (1990) *Protein Eng.* 3, 461–467.
4. McAllister, W. T. & Raskin, C. A. (1993) *Mol. Microbiol.* 10, 1–6.
5. Arnold, E., Ding, J., Hughes, S. H. & Hostomsky, Z. (1995) *Curr. Opin. in Struct. Biol.* 5, 27–38.
6. Ollis, D. L., Brick, P., Hamlin, R., Xuong, N. G. & Steitz, T. A. (1985) *Nature* (London) 313, 762–766.
7. Arnold, E., Jacobo-Molina, A., Nanni, R. G., Williams, R. L., Lu, X., Ding, J., Clark, A. D. J., Zhang, A., Ferris, A. L., Clark, P., Hizi, A. & Hughes, S. H. (1992) *Nature* (London) 357, 85–89.
8. Kohlstaedt, L. A., Wang, J., Rice, P. A., Friedman, J. M. & Steitz, T. A. (1993) in *Reverse Transcriptase*, eds. A. M. Skalka, S. P. Goff, (Cold Spring Harbor Laboratory Press), Plainview, N.Y. pp 223–250.
9. Davies, J. F. I., Almassy, R. J., Hostomsky, Z., Ferre, R. A. & Hostomsky, Z. (1994) *Cell* 76, 1123–1133.
10. Sousa, R., Chung, Y. J., Rose, J. P. & Wang, B. C. (1993) *Nature* 364, (London) 593–599.
11. Pelletier, H., Sawaya, M. R., Kuman, A., Wilson, S. H. & Kraut, J. (1994) *Science* 264, 1891–1903.
12. Unge, T., Knight, S., Bhikhabhai, R., Lovgren, S., Dauter, Z., Wilson, K. & Strandberg, B. (1994) *Structure* (London) 2, 953–961.
13. Sawaya, M. R., Pelletier, H., Kumar, A., Wilson, S. H. & Kraut, J. (1994) *Science* 264, 1930–1935.
14. Georgiadis, M. M., Jessen, S. M., Ogata, C. M., Telesnitsky, A., Goff, S. P. & Hendrickson, W. A. (1995) *Structure* (London) 3, 879–892.
15. Rodgers, D. W., Gamblin, S. J., Harris, B. A., Ray, S., Culp, J. S., Hellmig, B., Woolf, D. J., Debouck, C. & Harrison, S. C. (1995) *Proc. Natl. Acad. Sci. USA* 92, 1222–1226.
16. Joyce, C. M. & Steitz, T. A. (1994) *Annu. Rev. Biochem.* 63, 777–822.
17. Johnson, K. A. (1993) *Annu. Rev. Biochem.* 62, 685–713.
18. Erie, D. A., Hajiseyedjavadi, O., Young, M. C. & von Hippel, P. H. (1993) *Science* 262, 867–873.
19. Baltimore, D. (1970) *Nature* 226, 1209–1211.
20. Temin, H. & Mizutani, S. (1970) *Nature* (London) 226, 1211–1213.
21. Skalka, A. M. & Goff, S. P. (1993) *Reverse Transcriptase* (Cold Spring Harbor Lab. Press, Plainview, N.Y.).
22. Telesnitsky, A. & Goff, S. P. (1993) in *Reverse Transcriptase*, eds. A. M. Skalka, S. P. Goff, (Cold Spring Harbor Lab. Press, Plainview, N.Y.), pp. 49–84.
23. Tantillo, C., Ding , J., Jacobo-Molina, A., Nanni, R. G., Boyer , P. L., Hughes, S. H., Pauwels, R., Andries, K., Janssen, P. A. J. & Arnold, E. (1994) *J. Mol. Biol.* 243, 369–387.
24. Patel, P. H., Jacobo-Molina, A., Ding, J., Tantillo, C., Clark, A. D. J., Rag, R., Nanni, R. G., Hughes, S. H. & Arnold, E. (1995) *Biochemistry* 34, 5351–5363.
25. Blain, S. W. & Goff, S. P. (1993) *J. Biol. Chem.* 268, 23585–23592.
26. Telesnitsky, A. & Goff, S. P. (1993) *Proc. Natl. Acad. Sci. USA* 90, 1276–1280.
27. Goff, S. P., Traktman, P. & Baltimore, D. (1981) *J. Virol.* 38, 239–248.
28. Blain, S. W. & Goff, S. P. (1995) *J. Virol.* 69, 4440–4452.
29. Steitz, T. A., Smerdon, S. J., Jäger, J. & Joyce, C. M. (1994) *Science* 266, 2022–2025.
30. Sousa, R. Padilla, R. (1995) *EMBO J.* 14, 4609–4621.
31. Prasad, V. R. & Goff, S. P. (1989) *J. Biol. Chem.* 264, 16689–16693.

What is claimed is:

1. A Moloney murine leukemia virus reverse transcriptase capable of polymerizing I) a deoxyribonucleotide;

ii) a ribonucleotide; or iii) one or more deoxyribonucleotide and one or more ribonucleotide, wherein the Moloney murine leukemia virus reverse transcriptase has an amino acid sequence identical to the amino acid sequence present in wild type Moloney murine leukemia virus reverse transcriptase except the amino acid at position 155 is valine.

2. A purified Moloney murine leukemia virus reverse transcriptase, wherein an amino acid corresponding to position 155 of a wild type Moloney murine leukemia virus reverse transcriptase is a valine.

3. The purified Moloney murine leukemia virus reverse transcriptase of claim 2 which is capable of polymerizing i) deoxyribonucleotides;

ii) ribonucleotides; or iii) one or more deoxyribonucleotides and one or more ribonucleotides.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

ATATAGCTTA AGGATGCCGT TTTCTGCCTG AGACTCCAC                      39

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

ATATAGCTTA AGATCAAGCA CAGTGTACCA                                30

(2) INFORMATION FOR SEQ ID NO:3:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGTTCCTACC GGCC                                                        14

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CCAAGGATGG CCGGATC                                          17

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AAGCCCCACA TACAGAG                                          17

(2) INFORMATION FOR SEQ ID NO:6:

(i) SEQUENCE CHARACTERISTICS:

```
    (A) LENGTH: 28 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:6:

TTCGGGGTGT ATGTCTCTGA CAACCTGG                                              28
```